(12) United States Patent
Makhlouf

(10) Patent No.: US 9,730,741 B2
(45) Date of Patent: Aug. 15, 2017

(54) TEMPORARILY SECURED BONE REDUCTION CLAMP

(71) Applicant: Monsour Vincent Makhlouf, Glenview, IL (US)

(72) Inventor: Monsour Vincent Makhlouf, Glenview, IL (US)

(*) Notice: Subject to any disclaimer, the term of this patent is extended or adjusted under 35 U.S.C. 154(b) by 462 days.

(21) Appl. No.: 14/327,540

(22) Filed: Jul. 9, 2014

(65) Prior Publication Data

US 2016/0008041 A1 Jan. 14, 2016

Related U.S. Application Data

(60) Provisional application No. 61/921,914, filed on Dec. 30, 2013.

(51) Int. Cl.

| | |
|---|---|
| *A61B 17/04* | (2006.01) |
| *A61B 17/84* | (2006.01) |
| *A61F 2/08* | (2006.01) |
| *A61B 17/80* | (2006.01) |
| *A61B 17/88* | (2006.01) |
| *A61B 17/17* | (2006.01) |
| *A61B 17/68* | (2006.01) |
| *A61B 17/64* | (2006.01) |

(52) U.S. Cl.
CPC .......... *A61B 17/8019* (2013.01); *A61B 17/17* (2013.01); *A61B 17/8866* (2013.01); *A61B 17/6466* (2013.01); *A61B 2017/681* (2013.01)

(58) Field of Classification Search
None
See application file for complete search history.

(56) References Cited

U.S. PATENT DOCUMENTS

| | | |
|---|---|---|
| 2,427,128 A | 9/1947 | Ettinger |
| 2,460,470 A | 2/1949 | Rodgers |
| 2,507,710 A | 5/1950 | Grosso |
| 2,583,896 A | 1/1952 | Siebrandt |
| 3,477,429 A | 11/1969 | Sampson |
| 5,133,715 A | 7/1992 | Lenzo |
| 5,578,032 A | 11/1996 | Lalonde |
| 5,697,933 A | 12/1997 | Gundlapalli et al. |
| 5,725,532 A | 3/1998 | Shoemaker |

(Continued)

FOREIGN PATENT DOCUMENTS

EP 2689737 A1 1/2014

*Primary Examiner* — Sameh Boles
(74) *Attorney, Agent, or Firm* — Sukovic Law PC; Milena Sukovic

(57) ABSTRACT

In one embodiment of the disclosure, a bone reduction clamp includes a first and second detachable clamp arm, each including a first handle and a first base portion. The first clamp arm and the second clamp arm temporarily become secured together with an unfixed pivot post. The unfixed pivot post is unfixed between the first detachable clamp arm and the second detachable clamp arm. The first clamp arm includes a first base portion including a first extender and a first tip portion secured together with a first unfixed joint. The first tip portion includes one or more first tip portion guide edges. The first detachable clamp arm includes a first ratcheted tooth member extending from detachable clamp arm, to attach with a second ratcheted tooth member extending from the second detachable clamp arm.

13 Claims, 3 Drawing Sheets

(56) References Cited

U.S. PATENT DOCUMENTS

| | | | |
|---|---|---|---|
| 5,797,919 | A | 8/1998 | Brinson |
| 7,189,234 | B2 | 3/2007 | Zucherman et al. |
| 7,722,625 | B2 | 5/2010 | Sanders et al. |
| 7,806,899 | B2 | 10/2010 | Hogg et al. |
| 8,080,045 | B2 | 12/2011 | Wotton |
| 8,162,996 | B2 | 4/2012 | Schelling |
| 8,182,488 | B2 | 5/2012 | Oliver |
| 8,313,492 | B2 | 11/2012 | Wong et al. |
| 8,562,681 | B2 | 10/2013 | Shepard et al. |
| 8,579,950 | B1 | 11/2013 | Jordan |
| 2004/0024319 | A1 | 2/2004 | Flipo |
| 2006/0142777 | A1* | 6/2006 | Bastian ................ A61B 17/158 606/88 |
| 2008/0177297 | A1 | 7/2008 | Steiner et al. |
| 2009/0281582 | A1 | 11/2009 | Villa et al. |
| 2014/0012338 | A1 | 1/2014 | Kirschman |
| 2014/0031882 | A1 | 1/2014 | Schmuck et al. |

* cited by examiner

TEMPORARILY SECURED BONE REDUCTION CLAMP

This application claims the benefit of U.S. Provisional Application No. 61/219,914, filed Dec. 30, 2013, which is hereby incorporated by reference in its entirety.

FIELD OF THE DISCLOSURE

The present disclosure relates generally to bone reduction clamps and more particularly to a temporarily secured bone reduction clamp.

BACKGROUND

Existing bone reduction clamps are designed for reducing larger bones. Existing bone reduction clamps have narrow points of contact. When a bone fracture is comminuted (multiple small fragments) or transverse (perpendicular to the axis of the bone), narrow points of contact do not hold bone fragments well. Existing bone reduction clamps have a two-point contact, and so at best hold two bone fragments together. If there are three or more bone fragments, two points cannot stabilize the fragments well.

Existing bone reduction clamps, which do not have a two-point contact, have too large of a surface area in contact with the bone, so that too much of the bone is exposed during surgery. Existing bone reduction clamps require too much exposure of a bone when placing the clamp, thus requiring extra dissection, which negatively affects bone healing. Existing bone reduction clamps are cumbersome to position during surgery.

SUMMARY

In one embodiment of the disclosure, a bone reduction clamp includes a first and second detachable clamp arm, each including a first handle and a first base portion. The first clamp arm and the second clamp arm temporarily become secured together with an unfixed pivot post. The unfixed pivot post is unfixed between the first detachable clamp arm and the second detachable clamp arm. The first clamp arm includes a first base portion including a first extender and a first tip portion secured together with a first unfixed joint. The first tip portion includes one or more first tip portion guide edges. The first detachable clamp arm includes a first ratcheted tooth member extending from detachable clamp arm, to attach with a second ratcheted tooth member extending from the second detachable clamp arm.

BRIEF DESCRIPTION OF THE DRAWINGS

The described embodiments and other features, advantages and disclosures contained herein, and the manner of attaining them, are apparent to one of ordinary skill in the art. The present disclosure will be better understood by reference to the following description of various exemplary embodiments of the present disclosure taken in conjunction with the accompanying drawings, wherein.

DETAILED DESCRIPTION OF THE PREFERRED EMBODIMENTS

Figure 1:
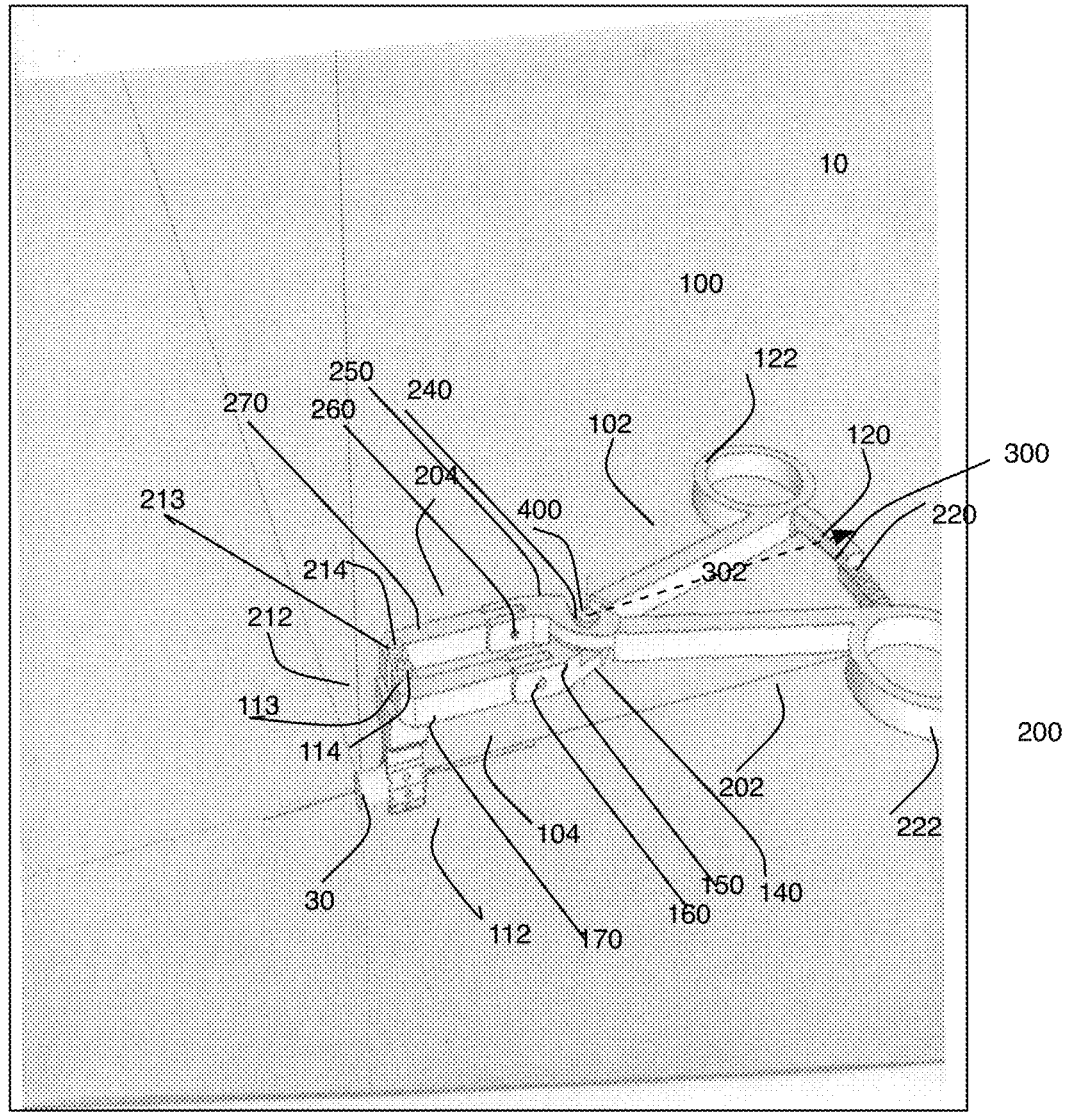
FIG. 1 illustrates an embodiment of a bone reduction clamp.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

There is a need for a bone reduction clamp that is capable of restoring smaller bones to the normal place or relation of parts and thereby reducing smaller bones or bones that have comminuted fractures or transverse fractures. There is a need for a bone reduction clamp that is capable of restoring bones with less exposure during surgery. There is a need for a bone reduction clamp that requires less exposure of a bone when placing the clamp. There is a need for a bone reduction clamp that is less cumbersome to position during surgery. Some embodiments of the disclosure herein enable some of the above needs to be realized.

FIG. 1 illustrates an embodiment of a bone reduction clamp 10. In an embodiment, the bone reduction clamp 10 may include a first detachable clamp arm 100 that may be attached to a second detachable clamp arm 200. The first detachable clamp arm 100 may include a first handle 102 and a first base portion 104. Detachable herein includes the definition that the clamp arm may be removed from the other. In an embodiment, detachable herein includes the definition that the clamp arm may be removed from the other by unhooking ratcheted tooth members (e.g., 120, 220) from being interlocked. In an embodiment, detachable herein includes the definition that the clamp arm may be removed from the other by sliding a base portion (e.g., 104 204) off from a tip portion (e.g., 112, 212). In an embodiment, detachable herein includes the definition that the clamp arm includes detachable parts that may be detached so that there is less exposure of a bone when placing or removing the clamp.

The second detachable clamp arm 200 may include a second handle 202 and a second base portion 204. In an embodiment, the first detachable clamp arm 100 and the second detachable clamp arm 200 may allow for each separate clamp arm and its associated parts to be placed around a problem bone independently from the other separate clamp arm and its associated parts. In an embodiment, detachable parts of each clamp arm may allow for more independent placement during surgery. In an embodiment, detachable parts of each clamp arm may allow for less invasive surgery. In an embodiment, a separate and detachable clamp arm and associated detachable parts may allow for better use or less invasive use during surgery that may be performed percutaneously (done through the skin) or with open reduction (exposing the skeletal parts).

The first detachable clamp arm 100 and the second detachable clamp arm 200 may be configured to be temporarily secured together with an unfixed pivot post 400. The unfixed pivot post 400 may be unfixed between the first detachable clamp arm 100 and the second detachable clamp arm 200. In an embodiment, the unfixed pivot post 400 may become secured by pivot post holders (e.g., 140, 240). In an embodiment, the unfixed pivot post 400 may become secured by pivot post holders (e.g., 140, 240) when tip portions (e.g., 112, 212) are secured around a bone 30 and when ratcheted tooth members (e.g., 120, 220) are interlocked. In an embodiment, the unfixed pivot post 400 may be temporarily secured, to position against both clamp arms 100, 200. In an embodiment, tension may hold the unfixed pivot post 400 to be temporarily secured when a first ratcheted tooth member 120 may be attached with the second ratcheted tooth member 220.

In the following embodiments of a detachable clamp arm (e.g., 100, 200), a single clamp arm is described with example element identifiers that may be referred to as a first or second corresponding element. In some embodiments of the first and second respective clamp arm, all elements may be similar. In some embodiments of the first and second respective clamp arm, some elements may be similar and some elements may be different. In an embodiment, a first clamp arm 100 may have a respective bottom orientation whereby a first pivot post holder 140 is aligned below a second pivot post holder 240, while having a respective top orientation whereby a first ratcheted tooth member 120 is aligned atop a second ratcheted tooth member 220.

In an embodiment, a detachable clamp arm (e.g., 100, 200) may include a handle (e.g., 102, 202), which may include a force application portion (e.g., 122, 222) and a ratcheted tooth member (e.g., 120, 220). In an embodiment, a detachable clamp arm (e.g., 100, 200) may include a base portion (e.g., 104, 204), which may be a single unit that extends from the handle (e.g., 102, 202) and a pivot post holder (e.g., 140, 240), lengthwise to a joint socket (e.g., 113, 213), which may hold an unfixed joint (e.g., 114, 214) of a tip portion (e.g., 112, 212) to temporarily secure the tip portion (e.g., 112, 212) to the detachable clamp arm (e.g., 100, 200).

In another embodiment, a base portion (e.g., 104, 204) may include more parts. In an embodiment, a base portion (e.g., 104, 204) may extend from the handle (e.g., 102, 202) and a pivot post holder (e.g., 140, 240), lengthwise to include a distal (e.g., distal from the bone 30 to be secured) base portion (e.g., 150, 250), a hinge pin (e.g., 160, 260), an extender base portion (e.g., 170, 270), and a tip portion (e.g., 112, 212). In an embodiment, the hinge pin (e.g., 160, 260) and extender base portion (e.g., 170, 270) may allow for less invasiveness or more range of motion of the clamp 10 during surgery than would a base portion made up of a single unit.

Figure 2:
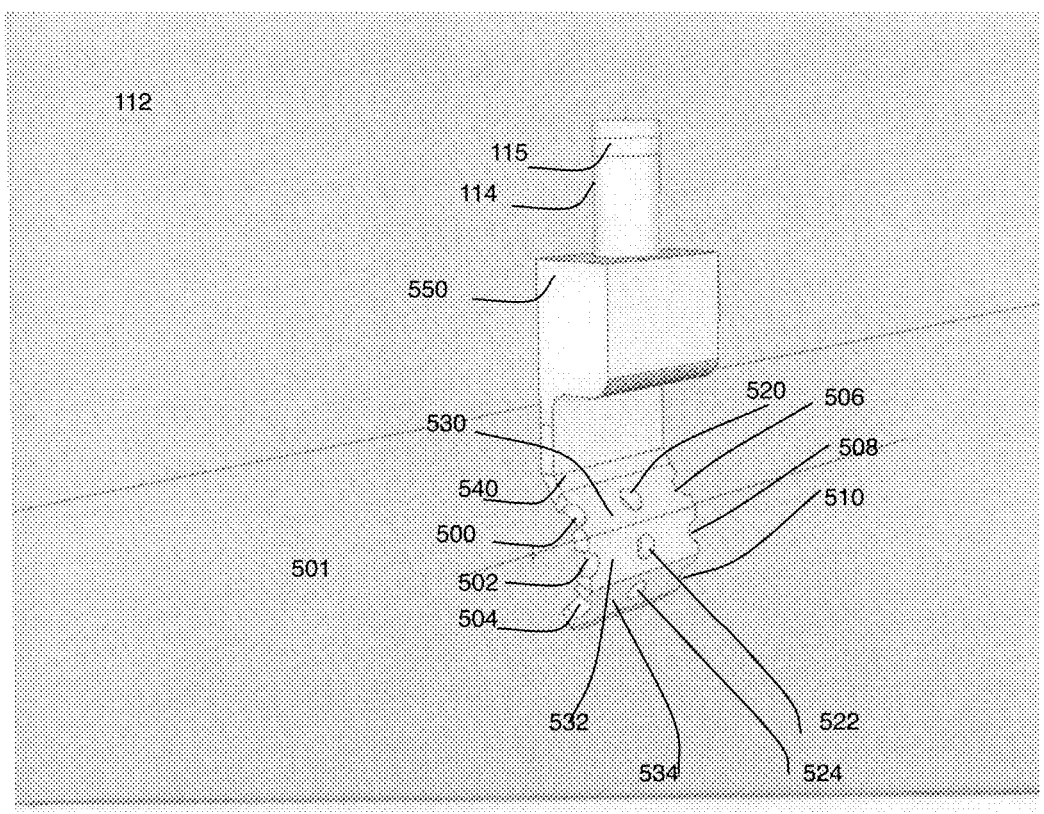
FIG. 2 illustrates an embodiment of a first tip portion that may be used in an embodiment of a bone reduction clamp.
Figure 3:
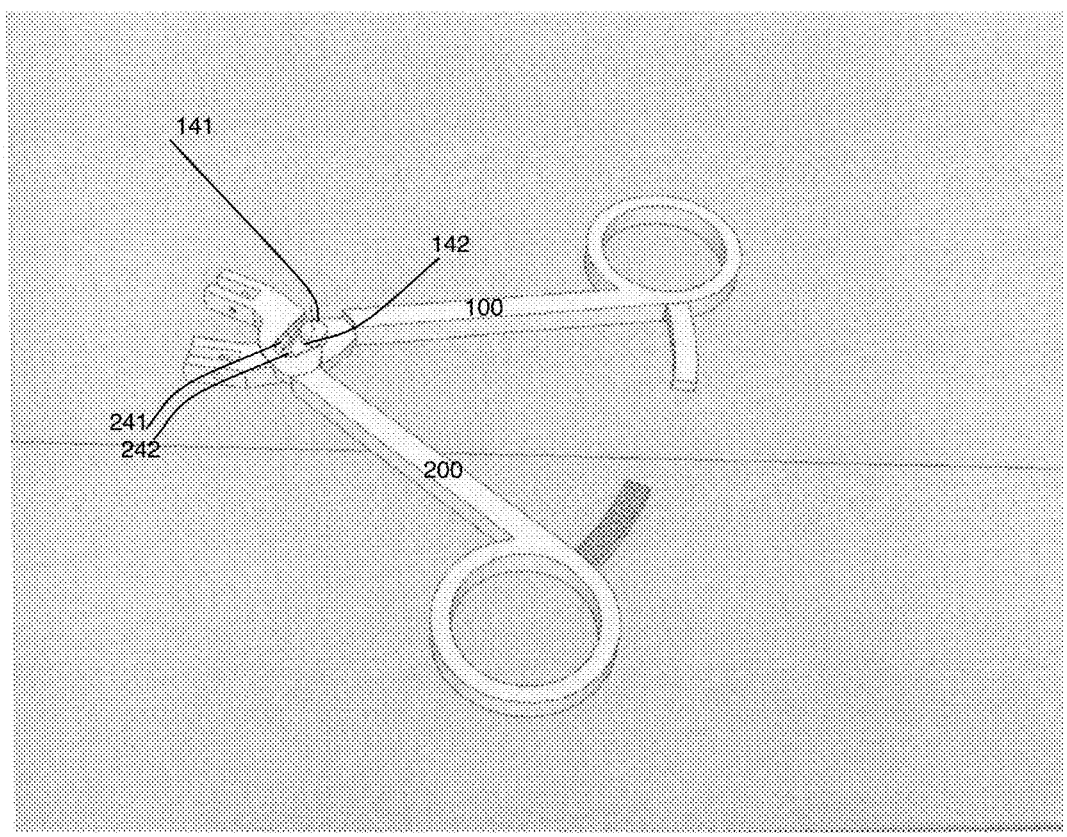
FIG. 3 illustrates an embodiment of a first detachable clamp arm that has an unfixed pivot post affixed thereon, and a second detachable clamp arm that has a pivot post receiver for temporarily holding the unfixed pivot post thereto.

In some embodiments of the first and second respective clamp arm, some elements may be similar and some elements may be different. For example, the first pivot post holder 140 and second pivot post holder 240 elements may be different types of holder embodiments. Example different embodiments of the first pivot post holder 140 and second pivot post holder 240 are illustrated in FIG. 3. In another example, a first tip portion 112 and a second tip portion 212 may be different. An example embodiment of a first tip portion 112 is illustrated in FIG. 2. Other embodiments of corresponding but differing elements are included with the description herein, but it is impractical to list all of them.

Referring back to FIG. 1, the first detachable clamp arm 100 may attach to the second detachable clamp arm 200 after a user has fitted a first tip portion 112 and a second tip portion 212 around a bone in need of reduction 30 and has secured the first tip portion 112 by temporarily fixing a first unfixed joint 114 of the first tip portion 112 to a first base portion 104 of the first detachable clamp arm 100, and has secured the second tip portion 212 by temporarily fixing a second unfixed joint 214 of the second tip portion 212 to a second base portion 204 of the second detachable clamp arm 200.

In an embodiment, both clamp arms 100, 200 may be temporarily secured to reduce the bone in need of reduction 30. In an embodiment, both clamp arms 100, 200 may be temporarily secured to each other and to a bone in need of reduction 30. In an embodiment, the first ratcheted tooth member 120 may extend from a first force application portion 122 of the first detachable clamp arm 100 and may extend along an arc line 300 substantially perpendicular to a radial direction 302 based from an unfixed pivot post 400. In this embodiment, the second ratcheted tooth member 220 of the second detachable clamp arm 200 may extend from the second force application portion 222 of the second detachable clamp arm 200 and may extend along the arc line 300 substantially perpendicular to the radial direction 302 based from the unfixed pivot post 400. The first ratcheted tooth member 120 and the second ratcheted tooth member 220 may form an interlocking surface area where one or more teeth meet to secure the bone reduction clamp 10 in place against the bone 30 and thereby also temporarily secure the unfixed pivot post 400 between the first detachable clamp arm 100 and the second detachable clamp arm 200.

In another embodiment, the first and second ratcheted tooth members 120, 220 may be attached at an angle not substantially perpendicular to the radial direction 302 based from the unfixed pivot post 400. For example, the angle from the radial direction 302 may be substantially 45 degrees or any angle between 0 degrees and 180 degrees (e.g., a 90 degree angle would be perpendicular to the radial direction 302). In the case where the angle may be different than perpendicular, then the teeth groves of the first and second ratcheted tooth members 120, 220 may be designed to compensate for the angle to result in an interlocking surface area between the first ratcheted tooth member 120 and the second ratcheted tooth member 220.

In an embodiment, the bone reduction clamp 10 may have one or more teeth of the first ratcheted member 120 configured to attach to one or more teeth of the second ratcheted member 220 to result in attached teeth, wherein the attached teeth may be set in a position that secures the unfixed pivot post 400 with the first clamp arm 100 and the second clamp arm 200, so that the first and second tip portions 112, 212 of the clamp 10 are in a secured position configured to be set around a bone in need of reduction 30. In an embodiment, the bone reduction clamp 10 may include a surface area of the one or more teeth of the first ratcheted member 120 that meets against a surface area of the one or more teeth of the second ratcheted member 220 so that the bone reduction clamp 10 is set in a position that has the first 112 and second tip portions 212 secured around a bone in need of reduction 30.

As stated above, other embodiments of corresponding but differing elements are included with the description herein, but it is impractical to list all of them. For example, FIG. 2 illustrates an embodiment of a first tip portion 112. In an embodiment, the size of a first tip portion 112 or a grabber 501 or both may correspond to the size of the bone in need of reduction or may be configured to correspond to the size of the bone in need of reduction 30.

A grabber 501 may provide a bone securing surface area. In an embodiment, a grabber 501 has a width of about 1.2 cm. In an embodiment, a grabber 501 has a width of about 1 cm. In an embodiment, a grabber 501 has any width falling around or between 1 cm. to 1.2 cm. In an embodiment, a grabber 501 has a width about or below 24, or 25 mm. Other sizes of the grabber 501 are included, so that, for example, its width, length, depth, shape, surface area or other dimension will correspond to the size of the bone in need of reduction 30. In an embodiment, "correspond to the size of the bone in need of reduction" includes the definition that the sizes of the grabber 501 components of the first tip portion 112 produce a bone securing surface area that fits against a surface area that is anywhere between one tenth to one half of the outer surface area of the size of the bone in need of reduction 30.

FIG. 2 may illustrate each of a first or second tip portion 112, 212 that may be used in an embodiment of the temporarily secured bone reduction clamp 10. In an embodiment, a second tip portion 212 and its elements may be similar to the first tip portion 112 and its elements. In an embodiment, a second tip portion 212 and its elements may be different to the first tip portion 112 and its elements. In an embodiment, the clamp 10 and its detachable parts may be used to reduce bones of an animal. In an embodiment, the clamp 10 and its detachable parts may be used to reduce bones of a human. In an embodiment, the clamp 10 and its detachable parts may be used to reduce bones on the hand or foot of an adult or child. Depending upon the bone in need of reduction 30, a correspondingly sized embodiment of a set of a first tip portion 112 and a second tip portion 212 is used with the clamp 10. The clamp 10 may be used with different sets of embodiments of a set of a first tip portion 112 and a second tip portion 212 so that the parts of the clamp 10, other than the first set of tip portions 112, 212, may be reused with a second set and third set and so on of tip portions 112, 212. In an embodiment, a clamp 10 with a first set of a first tip portion 112 and a second tip portion 212 may be used for a first operation, and the same clamp 10 may used with a second set of tip portions 112, 212 for a second operation. The first and second operation may reuse the clamp 10 with different sets of tip portions 112, 212 used specifically for each operation. In an embodiment, the clamp 10 may be used on a first operation on a first bone in need of reduction 30, which may be a first hand bone. The clamp 10 may be reused with a second set of tip portions 112, 212 for a second operation performed on a hand bone of a different person at a later time, on a second bone in need of reduction 30. In an embodiment, the clamp 10 may be used on a first operation on a first bone in need of reduction 30, which may be a first hand bone. The clamp 10 may be reused with a second set of tip portions 112, 212 for a second operation performed on a foot bone of a different person at a later time, on a second bone in need of reduction 30. In an embodiment, a set of the first tip portion 112 and the second tip portion 212 may be designed for a single use or may be disposable. In an embodiment, a set of the first tip portion 112 and the second tip portion 212 may be made of plastic. In an embodiment, a set of the first tip portion 112 and the second tip portion 212 may be made of recyclable plastic. In an embodiment, a set of the first tip portion 112 and the second tip portion 212 may be made of translucent plastic or radiolucent material.

In an embodiment, the first tip portion 112 may have one or more first tip portion guide edges (e.g., 500, 502, 504, 506, 508, 510). A guide edge may help a user by providing a guide surface area to be a guide for k-wire or screw placement. In an embodiment, the first tip portion 112 may have one or more guide grooves (e.g., 520, 522, 524). A guide groove may help a user by providing more surface area than a guide edge to provide a guide for k-wire or screw placement. A guide edge or guide groove may be part of a grabber portion 501 of the tip portion 112. In an embodiment, a guide edge or a guide groove are configured to guide a 1 mm or 1.2 mm diameter k-wire or screw. In an embodiment, a guide edge or a guide groove are configured to guide about a 1 mm or 1.2 mm diameter k-wire or screw, or up to a 2 mm. diameter k-wire or screw.

In an embodiment, the grabber 501 may have a continuous curve shaped surface area (not shown). In an embodiment, the grabber 501 may be made up of one or more blade plates (e.g., 530, 532, 534) adjacent to each other to form a substantially curved bone securing surface area. A grabber 501 may include a more general bone surface retainer section, such as a blade plate 530 or other geometry, such as a curved section (not shown). In an embodiment, the grabber portion 501 may have one or more respective surface areas to contact with or stabilize transverse or comminuted fractures of the bone. In an embodiment, the respective surface areas may include protuberances or nubbings. In an embodiment, the protuberances or nubbings may be configured to reduce tissue damage.

In an embodiment, the first tip portion 112 may include a first stabilizer portion 550 and the second tip portion 212 may include a second stabilizer portion to assist in directing contact with the bone in need of reduction 30. In an embodiment, stabilizer portion 550 may include a weighted portion with a wide surface area that runs parallel to the long axis of a bone in need of reduction 30, and that tapers in depth as it nears the grabber portion 501. In an embodiment, a transition section 540 may be used to couple the grabber portion 501 with the stabilizer portion 550. In an embodiment, the first tip portion 112 may include a first unfixed joint 114. In an embodiment, the first unfixed joint 114 may have a first groove 115. In an embodiment, the first groove 115 may be used to secure the first unfixed joint 114, after the first unfixed joint 114 is passed through a first joint socket 113 of the first base portion 104, by wrapping a flexible wrapper device around the groove 115. In an embodiment, the flexible wrapper device may be a wire or string or other pliable material.

In an embodiment, the bone reduction clamp 10 or portions thereof may be made of a radiolucent material, or a plastic material, or a metal material, or a combination of one or more of a radiolucent material or a plastic material or a metal material, or another material that is not a radiolucent material or a plastic material or a metal material.

FIG. 3 illustrates an embodiment of a clamp 10 including a first detachable clamp arm 100 that has an unfixed pivot post 400 (unfixed with respect to both clam arms 100, 200) that is affixed to a single arm, e.g., 100. In an embodiment, the first pivot post holder 140 is of a type, which is a single arm affixed pivot post 141. In this embodiment, a second detachable clamp arm 200 has a pivot post holder 240, which is of a type, which is designed to temporarily secure the unfixed pivot post 400 thereto. For example, in an embodiment, the second pivot post holder 240 may be a pivot post receiver 241 for temporarily holding the unfixed pivot post 400 thereto. In an embodiment, a pivot post receiver 241 may include a holding section 242 upon which a portion of a jutting section 142 of an affixed pivot post 141 may slide and rest upon temporarily.

In hand surgery bone clamps have narrow points of contact. When a fracture is comminuted (multiple small fragments) or transverse (perpendicular to the axis of the bone) narrow points of contact do not hold the fragments well.

Two-point contact would at best hold 2 bones. If you have 3 or more they cannot be stabilized by 2 points. The 2 points cannot be in line with the fracture but if the fracture is transverse this is what happens.

The parts of the clamps are placed separately for ease of application, then connected. The contact between clamp and bone is a surface instead of two points. There are spots to allow the pins aimed at stabilizing the broken bones to be placed at the angle desired.

As stated above, in hand surgery bone clamps have narrow points of contact. When a fracture is comminuted (multiple small fragments) or transverse (perpendicular to the axis of the bone) narrow points of contact do not hold the fragments well. The example embodiment claimed here solves this problem.

This clamp has plates for contact surfaces and the bone fragments are held in a stable configuration. The clamp is designed to be placed easily and through a small incision. The clamps allows for placement of pins at any angle needed.

The claimed example embodiment differs from what currently exists. Bone clamps are usually made of two components always attached to each other, they end in a sharp point that makes contact with the bone.

Cumbersome to Apply and Ineffective

The parts of the clamps are placed separately for ease of application, then connected. The contact between clamp and bone is a surface instead of two points. There are spots to allow the pin to be placed at the angle desired.

The Version (i.e., an Example Embodiment) of the Invention Discussed Here Includes:
 1. Grabber
 2. Connector
 3. Clamp one side
 4. Clamp the other side
 Relationship Between the Components:
 One half of the clamp is made of part 1, 2 3 the other part is made of 1, 2, 4
 How the Example Embodiment Works:
 One grabber with its half of the clamp is place on one side of the fracture. The other grabber is placed opposite. The clamp components are connected at the post. The bones are reduced in place with traction and manipulation of the parts. The clamp is closed at the base where the loops are and the whole fracture is stabilized and X-ray take to check. Next "pins" are drilled between the bone fragments to keep them in place, and the clamp removed.
 How to Make the Example Embodiment:
 3D printing or have a surgical instrument manufacturer to make it. All the elements are necessary.
 We can have different size grabbers for different size of bones and to use the clamp without exposing the fracture (closed reduction). The grabber can be made in hard radiolucent plastic to allow the X-ray to show the reduction better. The surface of the grabber can have small nubbings to minimize tissue damage.
 How to Use the Example Embodiment:
 The surgeon would need to have a set sterile, and use common surgical techniques.
 Additionally: In other than hand fractures, and in situations where exposure is tight and placing a clamp or a surgical instrument is cumbersome placing it in two separate parts that are later connected might help.

Bone reduction clamp is disclosed. The parts of the clamps are placed separately for ease of application, then connected. The contact between clamp and bone is a surface instead of two points. There are spots to allow the pin to be placed at the angle desired.

The foregoing is merely illustrative of some embodiments of the present disclosure and those skilled in the art can make various modifications without departing from the scope and spirit of the present disclosure.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed:

1. A bone reduction clamp comprising: a first detachable clamp arm including a first handle and a first base portion; a second detachable clamp arm including a second handle and a second base portion, the first clamp arm and the second clamp arm configured to temporarily become secured together with an unfixed pivot post, wherein the unfixed pivot post is unfixed between the first detachable clamp arm and the second detachable clamp arm, wherein the first detachable clamp arm has the unfixed pivot post affixed thereon, and the second detachable clamp arm has a pivot post receiver for temporarily holding the unfixed pivot post thereto; the first clamp arm including a first base portion; the first base portion including a first extender and a first tip portion, secured together with a first unfixed joint; the second clamp arm including a second base portion; the second base portion including a second extender and a second tip portion, secured together with a second unfixed joint; the first tip portion including plurality of first tip portion guide edges; the first detachable clamp arm including a first ratcheted tooth member extending from the first detachable clamp arm, to attach with a second ratcheted tooth member extending from the second detachable clamp arm.

2. The bone reduction clamp of claim 1 wherein the one or more teeth of the first ratcheted member are configured to attach to one or more teeth of the second ratcheted member of the bone reduction clamp to result in attached teeth, wherein the attached teeth are set in a position that secures the unfixed pivot post with the first clamp arm and the second clamp arm, and secures the first unfixed joint to be secured with the first clamp arm, and secures the second unfixed joint to be secured with the second clamp arm, so that the first and second tip portions of the clamp are in a secured position configured to be set around a bone.

3. The bone reduction clamp of claim 1 wherein a surface area of the one or more teeth of the first ratcheted member meet against a surface area of the to one or more teeth of the second ratcheted member so that the bone reduction clamp is set in a position that has the first and second tip portions secured around a bone.

4. The bone reduction clamp of claim 3 wherein the first and second tip portions each include a respective grabber portion including one or more bone surface retainer sections including one or more respective surface areas to stabilize transverse or comminuted fractures of the bone.

5. The bone reduction clamp of claim 3 wherein the first tip portion includes a first stabilizer portion and the second tip portion includes a second stabilizer portion to assist in directing contact with the bone.

6. The bone reduction clamp of claim 1 wherein the first an second tip portion includes respective blade plates each including respective surface areas to contact with and stabilize transverse or comminuted fractures of the bone, wherein the respective surface areas include protuberances or nubbings.

7. The bone reduction clamp of claim 6 wherein each blade plate includes one or more guide edges.

8. The bone reduction clamp of claim 7 wherein each blade plate includes one or more guide grooves.

9. The bone reduction clamp of claim 1 wherein the first and second base portions each include a respective unfixed joint and proximal and distal base portions; wherein the proximal base portion includes the extender.

10. The bone reduction clamp of claim 1 wherein the clamp is made of a radiolucent material.

11. The bone reduction clamp of claim 1 wherein the clamp includes a radiolucent material.

12. The bone reduction clamp of claim 10 wherein the clamp includes a plastic or metal material.

13. A bone reduction clamp arm comprising: a first handle and a first base portion; the first clamp arm configured to be temporarily secured to a corresponding second clamp arm, configured to be temporarily secured with the second detachable clamp arm with an unfixed pivot post, wherein the unfixed pivot post is unfixed between the first detachable clamp arm and the second detachable clamp arm, wherein the unfixed pivot post is affixed to the first clamp arm and the second clamp arm has a pivot post receiver for temporarily holding the unfixed pivot post thereto; the first clamp arm including a first base portion; the first base portion including a first extender and a first tip portion secured together with a first unfixed joint; the first tip portion including plurality of first tip portion guide edges; the first detachable clamp arm including a first force application portion; the first detachable clamp arm including a first ratcheted tooth member extending from the first force application portion of the first detachable clamp arm, to attach with a second ratcheted tooth member extending from the second detachable clamp arm.

* * * * *